United States Patent [19]

Snader

[11] 4,160,021
[45] Jul. 3, 1979

[54] SUBSTITUTED 2H-PYRAN-2,6(3H)-DIONE DERIVATIVES

[75] Inventor: Kenneth M. Snader, Hatboro, Pa.

[73] Assignee: SmithKline Corporation, Philadelphia, Pa.

[21] Appl. No.: 885,142

[22] Filed: Mar. 10, 1978

Related U.S. Application Data

[63] Continuation-in-part of Ser. No. 799,625, May 23, 1977, abandoned.

[51] Int. Cl.$^2$ .................. A61L 9/04; A61K 31/35; C07D 309/16
[52] U.S. Cl. ................... 424/45; 424/283; 260/345.8 R; 260/345.7 R; 260/343.5
[58] Field of Search ............... 260/345.7 R, 345.8 R, 260/343.5; 424/283, 45

[56] References Cited

U.S. PATENT DOCUMENTS

| 4,015,009 | 3/1977 | Chakrin et al. | 424/283 |
| 4,017,633 | 4/1977 | Willis | 424/283 |
| 4,025,614 | 5/1977 | Snader et al. | 424/283 |
| 4,025,642 | 5/1977 | Snader et al. | 424/283 |
| 4,032,652 | 6/1977 | Chakrin et al. | 424/283 |

Primary Examiner—Nicky Chan
Attorney, Agent, or Firm—Joseph A. Marlino; Richard D. Foggio; William H. Edgerton

[57] ABSTRACT

Substituted 2H-pyran-2,6(3H)-dione derivatives useful in the treatment of allergic conditions are prepared by reaction of 3,5-diacetyl-4,6-dihydroxy-2H-pyran-2-one with an appropriate aniline.

17 Claims, No Drawings

SUBSTITUTED 2H-PYRAN-2,6(3H)-DIONE DERIVATIVES

This application is a continuation-in-part of copending Ser. No. 799,625 filed May 23, 1977 now abandoned.

This invention relates to substituted 2H-pyran 2,6(3H)-dione derivatives which are useful for inhibiting the symptoms of an allergic response resulting from an antigen-antibody reaction. More specifically, the compounds of this invention are believed to be effective by inhibiting the release and/or formation and release of pharmacologically active mediators such as histamine, serotonin and slow-reacting substance of anaphylaxis (SRS-A) from effector cells which are produced and/or released as a result of an interaction of antigen and specific antibody fixed to the cell surface (allergic reaction). These properties enable the subject compounds to be useful in various allergic diseases such as asthma, rhinitis and urticaria.

The compounds of this invention are represented by the following general structural formula:

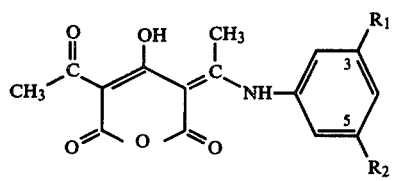

FORMULA I wherein:

$R_1$ represents lower alkoxy oxamoyl (—NHCOCOOR), hydroxyoxamoyl (—NHCOCOOH), lower alkoxy carbamoyl (—NHCOOR);

$R_2$ represents lower alkoxy oxamoyl, hydroxyoxamoyl, lower alkoxy carbamoyl and, when $R_1$ is lower alkoxy carbamoyl, $R_2$ is also hydrogen, and when $R_2$ is not hydrogen $R_1$ and $R_2$ are the same;

the lower alkoxy moieties (OR) have 1 or 2 carbon atoms.

Particular compounds of this invention represented by Formula I above are 3,5-bis-ethoxyoxamoyl, 3,5-bis-hydroxyoxamoyl 3,5-bis-ethoxycarbamoyl and 3-ethoxycarbamoyl.

The compounds of formula I are conveniently prepared as shown in the following scheme:

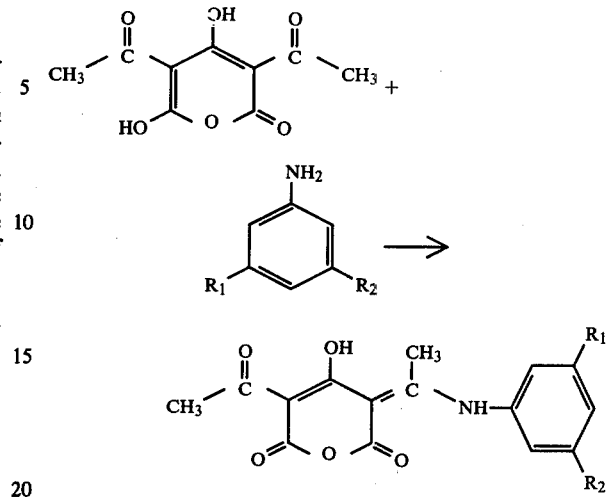

in which $R_1$ and $R_2$ are as defined above hydroxy but not oxamoyl. Thus, 3,5-diacetyl-4,6-dihydroxy-2H-pyran-2-one and the appropriately substituted aniline are heated at reflux in an inert organic solvent such as benzene, toluene, ethanol or methanol for from one to three hours to give the products.

To prepare the compounds of formula I wherein $R_1$ and $R_2$ are hydroxyoxamoyl, the corresponding lower alkoxy oxamoyl derivative is hydrolyzed by treatment with aqueous alkali metal hydroxide, such as sodium hydroxide, to obtain the hydroxyoxamoyl products.

Mono- and di-alkali metal salts of the compounds of formula I, such as the mono- and di-sodium or potassium salts are readily obtainable by treatment with the appropriate alkali metal alkoxide, for example methoxide, in an alkanol solvent such as methanol.

The pyran-2-one starting material indicated above is obtained by reaction of acetonedicarboxylic acid with acetic anhydride in sulfuric acid at elevated temperature. The reaction product actually has the tautomeric structure as shown below:

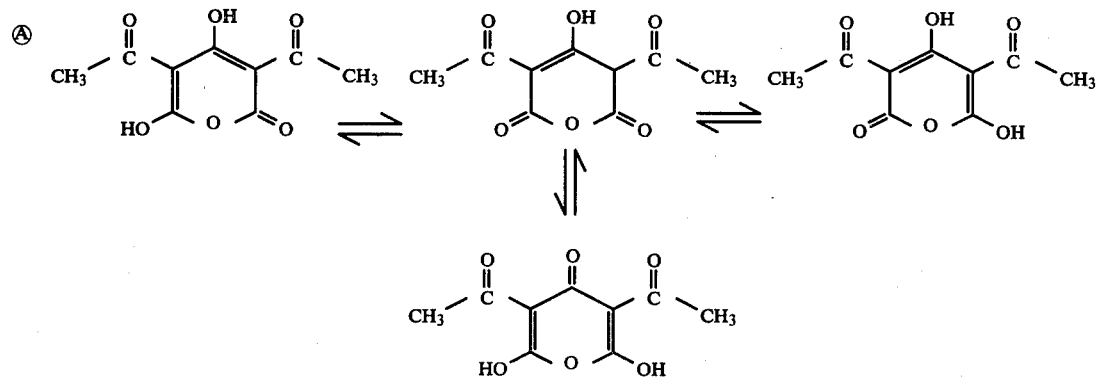

however for convenience it is designated herein as 3,5-diacetyl-4,6-dihydroxy-2H-pyran-2-one. Accordingly, the reaction of this product with an aniline as shown above gives a product having the tautomeric structures as shown below:

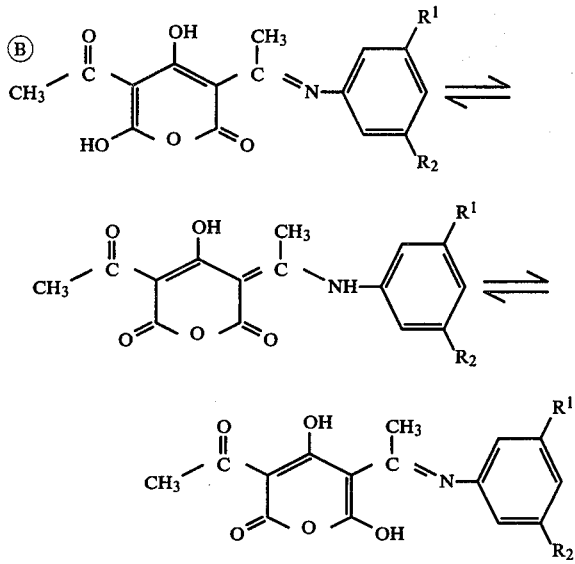

in which $R_1$ and $R_2$ are defined above for formula I. For convenience we have chosen to use one tautomeric form, namely the intermediate enamine pyran-2,6-dione structure, to represent all of the compounds formed by reaction of Ⓐ with the aniline, as indicated by formula I above. It will be apparent however to one skilled in the art that the more complete representation of the compounds of formula I is shown by the tautomerization Ⓑ.

The substituted aniline starting materials used herein are conveniently prepared by well-known preparative methods.

Wiley, R. H. et al. *J. Org. Chem.* 21:686-688 (1956) has reported the reaction of amines with the reaction product of acetonedicarboxylic acid and acetic anhydride, the latter designated 5-carboxydehydroacetic acid. Similarly, Kiang, A. K. et al. *J. Chem. Soc.* (c) pp. 2721-6 (1971) has disclosed such reaction products with amines. However there is no disclosure of products represented by formula I.

The inhibitory activity of the compounds of this invention on mediator release in sensitized tissues, thereby inhibiting the effects of the allergic reaction, is measured by the ability of the test compound to inhibit the passive cutaneous anaphylaxis (PCA) reaction in rats. In this test system, titered and appropriately diluted serum (from rats previously immunized by the intraperitoneal injection of ovalbuminaluminum hydroxide or ovalbumin-i.m.-*Bordatella pertussis* U.S.P. i.p.-and N-Brasiliensis i.p.) containing reaginic antibodies directed against ovalbumin is injected intradermally at four sites on the shaved backs of normal adult male rats. Forty-eight hours later the animals are injected intravenously with 0.5 ml. of isotonic saline solution containing 5 mg. of the ovalbumin antigen and 5 mg. of Evans blue dye. Chemical mediators such as histamine and serotonin which are released at the sensitized sites as a result of a local cellular anaphylaxis, cause an increase in capillary permeability with resultant leakage of plasma and formation of a wheal. The wheal is visualized by the plasma protein-bound Evans blue dye. Under conditions of the test, the average control wheal is approximately 12×12 mm. Thirty minutes following antigen challenge, the animals are killed, the dorsal skin is reflected and the diameter of the wheals recoded. A test compound is administered intravenously, initially at 0.5 minutes prior to antigen challenge (longer pretreatment times and other routes of drug administration, i.e. oral or intraperitoneal, may be employed). Percent inhibition is calculated from the difference in mean average wheal diameter between a treated group and saline or appropriate diluent controls.

The interruption by a test compound of the sequence of events triggered by reaginic antibody-antigen interaction on the surface of sensitized cells is indicative of utility in inhibiting the symptoms which result from an immediate-type allergic response.

The compounds of formula I administered intravenously to rats at doses of from 0.03125 to 10 mg/kg produce marked inhibition of the PCA reaction. For example, 5-acetyl-3-[1-(3,5-bis-ethoxyoxamoyl-phenylamino)ethylidene]-4-hydroxy-2$\underline{H}$-pyran-2,6(3$\underline{H}$)-dione produced 44% inhibition of the rat PCA wheal at 0.03125 mg/kg i.v. Another compound, 5-acetyl-3-[1-(3,5-bis-hydroxyoxamoylphenylamino)ethylidene]-4-hydroxy-2$\underline{H}$-pyran-2,6(3$\underline{H}$)-dione, produced 47% inhibition of the rat PCA wheal at 0.063 mg/kg, i.v.

The 5-acetyl-3-[1-(3,5-bis-ethoxycarbamoyl-phenylamino)-ethylidene]-4-hydroxy-2$\underline{H}$-pyran-2,6(3$\underline{H}$)-dione compound produced 97% inhibition of the PCA reaction at 0.5 mg/kg i.v. Further, 5-acetyl-3-[1-(3-ethoxycarbamoylphenylamino)ethylidene]-4-hydroxy-2$\underline{H}$-pyran-2,6(3$\underline{H}$)-dione produced 31% inhibition at 0.5 mg/kg i.v.

In testing for mechanism of action the compounds of formula I, following i.v. administration at the same dose and pretreatment time which exhibited significant inhibition of the rat 48-hour PCA reaction do not provide comparable inhibition of wheals of equal severity produced in rats by the intracutaneous administration of histamine and serotonin.

Upon oral administration, 5-acetyl-3-[1-(3,5-bis-ethoxyoxamoylphenylamino)ethylidene]-4-hydroxy-2$\underline{H}$-pyran-2,6-(3$\underline{H}$)-dione produced 76% inhibition in the rat 48-hour PCA system at 6.25 mg/kg and a pretreatment time of 15 minutes. In the same test for oral administration 5-acetyl-3-[1-(3-ethoxycarbamoyl-phenylamino)ethylidene]-4-hydroxy-2$\underline{H}$-pyran-2,6(3$\underline{H}$)-dione produced 82% inhibition at 3.13 mg/kg.

The compounds of this invention may be administered in conventional pharmaceutical compositions comprising an appropriate amount of a compound of formula I in association with a pharmaceutical carrier or diluent. The nature of the composition and the pharmaceutical carrier or diluent will of course depend upon the intended route of administration, i.e., orally, parenterally or by inhalation. Usually a compound is administered to an animal in a composition comprising an amount sufficient to produce an inhibition of the symptoms of an allergic response. When employed in this manner, the dosage of the composition is such that from 0.5 mg. to 500 mg. of active ingredient are administered at each administration. For convenience equal doses will be administered 1 to 4 times daily with the daily dosage regimen being about 0.5 mg. to about 2000 mg.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant such as dichlorodifluoromethane or chlorotrifluoroethane to be administered from a pressurized container. The compositions may also comprise the solid active ingredient diluted with a solid diluent, e.g. lactose, for administration from a powder inhalation device. In the above compositions, the amount of carrier or diluent will vary but preferably will be the major proportion of a suspension or solution of the active ingredient. When the diluent is a solid it may be present in less, equal or greater amounts than the solid active ingredient.

A wide variety of other pharmaceutical forms can be employed. Thus, if a solid carrier is used the preparation can be tableted, placed in a hard gelatin capsule in powder or pellet form, or in the form of a troche or lozenge for oral administration. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampul, or an aqueous or nonaqueous liquid suspension.

Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

The pharmaceutical preparations thus described are made following the conventional techniques of the pharmaceutical chemist involving mixing, granulating and compressing when necessary, or variously mixing and dissolving the ingredients as appropriate to the desired end product.

Included within the scope of this invention is the method of inhibiting the symptoms of an allergic response resulting from an antigen-antibody reaction which comprises administering to an animal a therapeutically effective amount for producing said inhibition of a compound of formula I, preferably in the form of a pharmaceutical composition. The administration may be carried out in dosage units at suitable intervals or in single doses as needed. Usually the method of this invention will be practiced when relief of allergic symptoms is specifically required. However, the method is also usefully carried out as continuous or prophylactic treatment. A particular application is a method of relieving or preventing allergic airway obstruction which comprises administering to an animal a therapeutically effective amount at suitable intervals. It is within the skill of the art to determine by routine experimentation the effective dosage to be administered from the dose range set forth above, taking into consideration such factors as the degree of severity of the allergic condition being treated, and so forth.

The following examples illustrate the preparation of compounds of formula I and their incorporation into pharmaceutical compositions and as such are not to be considered as limiting the invention set forth in the claims appended hereto.

EXAMPLE 1

A mixture of 3.5 g. (0.01 mol) of 1-nitro-3,5-bis-ethoxyoxamoylbenzene (prepared from 3,5-diaminonitrobenzene by reaction with ethoxyoxalyl chloride in pyridine) in 100 ml. of methanol was hydrogenated over 200 mg. of 10% palladium-on-carbon at 50 psi. Reduction was complete in 16 hours. To the mixture was added tetrahydrofuran (about 100 ml.) to dissolve the precipitate, the catalyst was filtered and to the filtrate containing 3,5-bis-ethoxyoxamoylaniline was added 2.12 g. (0.01 mol) of 3,5-diacetyl-4,6-dihydroxy-2H-pyran-2-one. This mixture was heated under reflux while 100 ml. of volatile solvent was collected by distillation. Heating was stopped, 50 ml. of methanol was added and the product collected by filtration, giving 5-acetyl-3-[3,5-bis-ethoxyoxamoylphenylamino)ethylidene]-4-hydroxy-2H-pyran-2,6(3H)-dione, m.p. 195° C.

Analysis Calculated: C, 53.39; H, 4.48; N, 8.12. Found: C, 53.11; H, 4.62; N, 8.21.

Similarly, employing 1-nitro-3,5-bis-methoxyoxamoylbenzene as the starting material described above furnishes the corresponding 5-acetyl-4-hydroxy-3-[1-(3,5-bis-methoxyoxamoylphenylamino)ethylidene]-2H-pyran-2,6(3H)-dione.

EXAMPLE 2

A solution of 1.5 g. (0.0029 mol) of 5-acetyl-3-[1-(3,5-bis-ethoxyoxamoylphenylamino)ethylidene]-4-hydroxy-2H-pyran-2,6(3H)-dione (prepared as in Example 1) in 200 ml. of water and 0.352 g. (0.009 mol) of sodium hydroxide was stirred at 25° C. for two hours. The solution was chilled and acidified with 3N hydrochloric acid to pH 2. The product was filtered, washed with water and dried to obtain 5-acetyl-4-hydroxy-3-[1-(3,5-bis-hydroxyoxamoylphenylamino)ethylidene]-2H-2,6(3H)-dione which did not melt by 325° C.

Analysis Calculated: C, 48.06; H, 3.71; N, 8.85. Found: C, 48.11; H, 3.89; N, 9.11.

As a specific embodiment of a composition of this invention, an active ingredient such as 5-acetyl-4-hydroxy-3-[1-(3,5-bis-hydroxyoxamoylphenylamino)ethylidene]-2H-pyran-2,6(3H)-dione is dissolved in sterile water at a concentration of 0.5% and aerosolized from a nebulizer operating at an air flow adjusted to deliver the desired aerosolized weight of drug.

For oral administration, a composition such as the following can be prepared.

| Ingredients | Mg./Tablet |
|---|---|
| 5-Acetyl-4-hydroxy-3-[1-(3,5-bis-ethoxyoxamoylphenylamino)ethylidene]-2H-pyran(3H)-dione | 10 |
| Calcium sulfate, dihydrate | 150 |
| Sucrose | 25 |
| Starch | 15 |
| Talc | 5 |
| Stearic acid | 3 |

The sucrose, calcium sulfate and active ingredient are thoroughly mixed and granulated with hot 10% gelatin solution. The wetted mass is passed through a #6 mesh screen directly onto drying trays. The granules are dried at 120° F. and passed through a #20 mesh screen, mixed with the starch, talc and stearic acid, and compressed into tablets.

EXAMPLE 3

A solution of 2.0 g. (0.0067 mol) of 3,5-bis-ethoxycarbamoylnitrobenzene in 150 ml. of 2B ethanol was hydrogenated over 200 mg. of 10% palladium-on-carbon at 50 psi. Reduction was complete in 1 hour, the catalyst was filtered, and to the colorless filtrate was added 1.42 g. (0.0064 mol) of 3,5-diacetyl-4,6-dihydroxy-2H-pyranone. The mixture was heated under reflux for 45 minutes, cooled and the product filtered to yield 5-acetyl-4-hydroxy-3-[1-(3,5-bis-ethoxycarbamoylphenylamino)ethylidene]-2H-pyran-2,6(3H)-dione, m.p. 234°–235° C.

Analysis Calculated: C-54.66; H, 5.02; N, 9.11. Found: C-54.72; H, 5.02; N, 9.15.

Similarly, employing 3,5-methoxycarbamoylnitrobenzene as the starting material described above yields the corresponding 5-acetyl-4-hydroxy-3-[1-(3,5-bis-methoxycarbamoylphenylamino)-ethylidene]-2H-pyran-2,6(3H)-dione.

EXAMPLE 4

A solution of 2.0 g. (0.0095 mol) of 3-ethoxycarbamoylnitrobenzene in 100 ml. of 2B ethanol was hydrogenated over 200 mg. of 10% palladium-on-carbon at 50 psi. Reduction was complete in 1 hour, the catalyst was filtered and to the filtrate was added 1.71 g. (0.0095 mol) of 3,5-diacetyl-4,6-dihydroxy-2H-pyranone. The mixture was heated under reflux for 1.5 hours, cooled, and the product filtered to yield 5-acetyl-4-hydroxy-3-[1-(3-ethoxycarbamoylphenylamino)ethylidene]-2H-pyran-2,6-(3H)-dione, m.p. 162°–164° C.

Analysis Calculated: C: 57.75; H: 4.85; N: 7.61. Found: C: 57.48; H: 4.78; N: 7.48.

What is claimed is:

1. A compound represented by the formula:

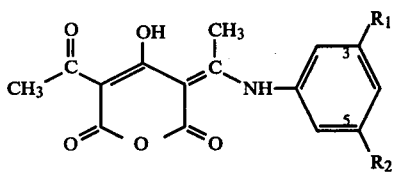

wherein:
$R_1$ is lower alkoxy oxamoyl, hydroxyoxamoyl, lower alkoxy carbamoyl;
$R_2$ is lower alkoxy oxamoyl, hydroxyoxamoyl, lower alkoxy carbamoyl, and when $R_1$ is lower alkoxy carbamoyl, $R_2$ is also hydrogen, and when $R_2$ is not hydrogen $R_1$ and $R_2$ are the same; and
the lower alkoxy moieties have 1 or 2 carbon atoms, or a mono- or di-alkali metal salt of said compound.

2. A compound according to claim 1 in which $R_1$ and $R_2$ are ethoxyoxamoyl.

3. A compound according to claim 1 in which $R_1$ and $R_2$ are hydroxyoxamoyl.

4. A compound according to claim 1 in which $R_1$ and $R_2$ are ethoxycarbamoyl.

5. A compound according to claim 1 in which $R_1$ is ethoxycarbamoyl and $R_2$ is hydrogen.

6. A pharmaceutical composition for inhibiting the symptoms of asthma comprising a nontoxic pharmaceutical carrier or diluent and an amount sufficient to produce said inhibition of a compound represented by the formula:

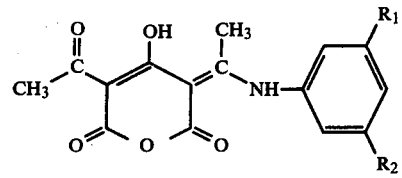

wherein:
$R_1$ is lower alkoxy oxamoyl, hydroxyoxamoyl, lower alkoxy carbamoyl;
$R_2$ is lower alkoxy oxamoyl, hydroxyoxamoyl, lower alkoxy carbamoyl, and when $R_1$ is lower alkoxy carbamoyl, $R_2$ is also hydrogen, and when $R_2$ is not hydrogen $R_1$ and $R_2$ are the same; and
the lower alkoxy moieties have 1 or 2 carbon atoms, or a mono- or di-alkali metal salt of said compound.

7. A pharmaceutical composition according to claim 6 in a form suitable for administration by inhalation.

8. A pharmaceutical composition according to claim 6 comprising a solution or suspension of the active ingredient in sterile water.

9. A pharmaceutical composition according to claim 6 in the form of an aerosol formulation.

10. A pharmaceutical composition according to claim 6 in which the pharmaceutical carrier or diluent is a solid.

11. A pharmaceutical composition according to claim 6 in which $R_1$ and $R_2$ are ethoxyoxamoyl.

12. A pharmaceutical composition according to claim 6 in which $R_1$ and $R_2$ are hydroxyoxamoyl.

13. A pharmaceutical composition according to claim 6 in which $R_1$ and $R_2$ are ethoxycarbamoyl.

14. A pharamceutical composition according to claim 6 in which $R_1$ is ethoxycarbamoyl and $R_2$ is hydrogen.

15. A pharmaceutical composition according to claim 6 in dosage unit form and in which the active ingredient is in an amount of from about 0.5 to about 500 mg. per dosage unit.

16. A method of inhibiting the symptoms of asthma which comprises administering to an animal in need of said inhibition a therapeutically effective amount for producing said inhibition of a compound represented by the formula:

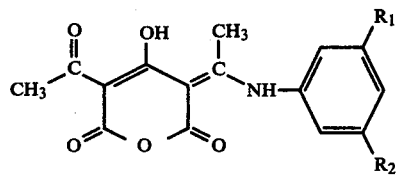

wherein:
$R_1$ is lower alkoxy oxamoyl, hydroxyoxamoyl, lower alkoxy carbamoyl;
$R_2$ is lower alkoxy oxamoyl, hydroxyoxamoyl, lower alkoxy carbamoyl, and when $R_1$ is lower alkoxy carbamoyl, $R_2$ is also hydrogen, and when $R_2$ is not hydrogen $R_1$ and $R_2$ are the same; and
the lower alkoxy moieties have 1 or 2 carbon atoms, or a mono-or di-alkali metal salt of said compound.

17. The method according to claim 16 in which the active ingredient is administered in a daily dosage regimen of from about 0.5 mg. to about 2000 mg.

* * * * *